United States Patent [19]

Chien et al.

[11] Patent Number: 4,690,683
[45] Date of Patent: Sep. 1, 1987

[54] TRANSDERMAL VARAPAMIL DELIVERY DEVICE

[75] Inventors: Yie W. Chien, North Brunswick; Kakuji Tojo, Highland Park, both of N.J.

[73] Assignee: Rutgers, the State University of New Jersey, New Brunswick, N.J.

[21] Appl. No.: 751,126

[22] Filed: Jul. 2, 1985

[51] Int. Cl.[4] .............................................. A61K 9/00
[52] U.S. Cl. .................................... 604/896; 128/156; 424/448; 424/449; 424/486
[58] Field of Search ................. 128/156; 604/891, 896, 604/897, 890; 424/19-24

[56] References Cited

U.S. PATENT DOCUMENTS

| | | |
|---|---|---|
| 2,693,438 | 11/1954 | Ward . |
| 3,279,996 | 10/1966 | Long, Jr. et al. . |
| 3,287,222 | 11/1966 | Larde et al. . |
| 3,545,439 | 12/1970 | Duncan . |
| 3,598,123 | 8/1971 | Zaffaroni ............................ 604/897 |
| 3,699,963 | 10/1972 | Zaffaroni ............................ 604/897 |
| 3,710,795 | 1/1973 | Higuchi et al. . |
| 3,731,683 | 5/1973 | Zaffaroni ............................ 604/897 |
| 3,734,097 | 5/1973 | Zaffaroni ............................ 604/897 |
| 3,792,951 | 7/1973 | Zaffaroni ............................ 604/897 |
| 3,797,494 | 3/1974 | Zaffaroni ............................ 604/897 |
| 3,946,106 | 3/1976 | Chien et al. . |
| 3,992,518 | 11/1976 | Chien et al. . |
| 3,996,934 | 12/1976 | Zaffaroni ............................ 604/897 |
| 4,031,894 | 6/1977 | Urquhart et al. ................... 604/897 |
| 4,053,580 | 10/1977 | Chien et al. . |
| 4,060,084 | 11/1977 | Chandrasekaran et al. ........ 604/897 |
| 4,210,633 | 7/1980 | Takruri et al. . |
| 4,286,592 | 9/1981 | Chandrasekaran ................ 128/156 |
| 4,291,015 | 9/1981 | Keith et al. . |
| 4,314,557 | 2/1982 | Chandrasekaran ................ 604/896 |
| 4,336,243 | 6/1982 | Sanvordeker et al. . |
| 4,379,454 | 4/1983 | Campbell et al. .................. 604/897 |
| 4,458,990 | 10/1985 | Mueller et al. ...................... 424/19 |
| 4,460,371 | 7/1984 | Abber ................................. 604/897 |
| 4,460,372 | 7/1984 | Campbell et al. .................. 604/897 |
| 4,461,759 | 7/1984 | Dunn .................................... 424/35 |
| 4,486,193 | 12/1984 | Shaw et al. ........................ 604/890 |

FOREIGN PATENT DOCUMENTS 0013606 7/1980 European Pat. Off. .
83/00091 1/1983 PCT Int'l Appl. .

OTHER PUBLICATIONS

Billups et al., *American Drug Index*, J. B. Lippincott Co., Philadelphia, 1983, p. 652.
Ciba, *The Transdermal Nitroglycerin Therapeutic System* (1981).
*American Pharmacy*, vol. NS22, No. 2, Feb. 1982, pp. 34-35.
Windheuser et al., *Journal of Pharmaceutical Sciences*, vol. 71, No. 11, Nov. 1982, pp. 1211-1213.
Chien, *Drug Development and Industrial Pharmacy*, 9(4), pp. 497-520 (1983).
Black, *U.S. Pharmacist*. Nov. 83, pp. 49-60.
*Chemical Week*, Sep. 26, 1984, pp. 42-46.

*Primary Examiner*—C. Fred Rosenbaum
*Assistant Examiner*—Jerome R. Smith, Jr.
*Attorney, Agent, or Firm*—Schwartz, Jeffery, Schwaab, Mack, Blumenthal & Evans

[57] ABSTRACT

A transdermal drug delivery device for administering 5-[(3,4-dimethoxyphenethyl) methylamino]-2-(3,4-dimethoxyphenyl)-2-isopropylvaleronitrile comprising a permeable matrix of silicone elastomer or other bioacceptable lipophilic polymer material having an effective cardiovascular affecting amount of active drug and an effective drug release promoting amount of a transport enhancing agent dispersed therein. The back of the matrix is covered with an occlusive backing and the face of the matrix is covered with a biocompatible adhesive such as a silicone adhesive also having a transport enhancing agent dispersed therein. A supply of skin permeation enhancing agent may be provided adjacent the adhesive layer such that the skin of a patient to whom the device is applied is pretreated with permeation enhancing agent. Particularly preferred skin permeation and transport enhancing agents include N,N-diethyl-m-toluamide, isopropyl myristate and similar compounds.

29 Claims, 2 Drawing Figures

TRANSDERMAL VARAPAMIL DELIVERY
DEVICE

BACKGROUND OF THE INVENTION

This invention relates to a device for transdermal administration of an active pharmaceutical at a sustained, substantially uniform rate of delivery over an extended period of time. More particularly, the invention relates to a device particularly adapted for transdermal administration of verapamil.

Treatment of patients with pharmaceutically active substances is commonly carried out by periodically adminstering defined doses of the pharmaceutical to the patient, e.g. either orally or by injection. Such techniques provide a maximum dosage of the pharmaceutical following each administration which then continually declines until the next dose is administered. In order to assure that an effective dosage of pharmaceutical is present in the body at all times, peak dosages which are much higher than the effective level are needed. This undesirably increases the amount of pharmaceutical which is consumed and concomitantly increases the danger of undesired side effects. Moreover, even though substantial excess dosages are adminstered, there is always a danger that the concentration of the pharmaceutical may drop below the effective level if adminstration of a subsequent dose is delayed or omitted. Further, there is a possibility, particularly with oral administration of pharmaceuticals, that a portion of the pharmaceutically active substance may be metabolized before reaching its intended locus of activity. This further increases the excess of pharmaceutical which must be administered in order to assure that an effective concentration is maintained.

Techniques also exist for sustained, low level administration of pharmaceuticals. The technique most commonly utilized is intravenous infusion. This technique, while effective at providing sustained low levels of pharmaceutical, is cumbersome and also requires close supervision by trained medical personnel. Consequently, intravenous infusion of pharmaceuticals typically requires hospitalization of the patient with attendant expense and inconvenience.

Techniques have also been developed for administering pharmaceuticals at sustained low levels by absorption through the skin. Transdermal delivery devices are now commercially available for nitroglycerin, scopolamine and other pharmaceuticals. Such devices typically comprise either a pharmaceutical-containing reservoir enclosed by a membrane through which the pharmaceutical can diffuse at a controlled rate or a dispersion of pharmaceutical in a polymer matrix from which the pharmaceutical can diffuse at a controlled rate. The devices are attached either adhesively or otherwise to the skin of a patient, and the pharmaceutical is permitted to diffuse from the device and permeate through the outer sublayers of skin until it is absorbed into the blood stream in the fine capillary network of the dermis. Once absorbed into the blood stream, the pharmaceutical is then carried throughout the entire body system of the patient.

While such transdermal delivery devices have worked well for some pharmaceuticals, notably nitroglycerine, conventional transdermal delivery devices have not proved suitable for other important drugs. Reservoir-type delivery devices are subject to the risk of undersirable dose damping if the rate controlling membrane is inadvertently damaged. The rate of release of some pharmaceuticals from conventional devices has proved to be too slow to provide an effective dosage of pharmaceutical unless the size of the transdermal delivery patch was excessively large. In some instances it has been difficult to maintain effective contact between the transdermal drug delivery device and the skin of the patient. Attempts to solve the problem of maintaining contact by providing an adhesive over the face of the delivery device so that it positively adheres to the patient's skin have not been fully successful. In some instances, due to the nature of the drug delivery matrix, available adhesives have not adhered well to the transdermal drug delivery device. Where satisfactory adhesion between the drug delivery device and the matrix has been obtained, it has been found that the adhesive acts as a barrier and retards transfer of the active substance from the drug delivery device to the skin. For some pharmaceuticals, the rate of skin permeation and absorption is so low that it has not been possible to provide an effective dosage within a reasonably sized area of skin.

One drug for which a transdermal delivery device would be desirable is 5-[(3,4-dimethoxy-phenethyl) methyl-amino]-2-(3,4-dimethoxyphenyl)-2-isopropyl-valeronitrile, also known as verapamil. This substance is a well established coronary vasodialator and antiarrythmic agent. A self-supporting polymeric diffusion matrix for sustained transdermal delivery of verapamil has been proposed by Keith et al. (PCT application No. WO83/00091), but this system is subject to many of the disadvantages discussed above.

SUMMARY OF THE INVENTION

Accordingly, it is the object of the present invention to provide a new drug delivery device for sustained uniform administration of a pharmaceutical by the transdermal route.

Another object of the present invention is to provide a transdermal drug delivery device which enables sustained maintenance of an effective dosage level using a lesser amount of active ingredient than required for periodic administration either orally or by injection.

A further object of the present invention is to provide a transdermal drug delivery device which is not subject to the danger of dose damping.

It is also an object of the present invention to provide a transdermal drug delivery device from which the active pharmaceutical is released at an enhanced rate.

A still further object of the present invention is to provide a transdermal drug delivery device in which effective contact between the device and the skin of a patient can be continuously maintained.

Yet another object of the present invention is to provide an adhesively attached transdermal drug delivery device in which the adhesive layer permits a high rate of transfer of active pharmaceutical from the device to the skin of a patient.

Additionally, it is an object of the present invention to provide a transdermal drug delivery device which facilitates permeation of the active pharmaceutical through the skin of a patient.

It is also an object of the present invention to provide a transdermal drug delivery device which can administer an effective dosage of pharmaceutical while at the same time being conveniently small in size.

These and other objects of the invention are achieved by providing a transdermal drug delivery device comprising a permeable bioacceptable lipophilic polymer matrix having an effective cardiovascular affecting amount of 5-[(3,4-dimethoxyphenethyl) methyl-amino]-2-(3,4-dimethoxyphenyl)-2-isopropylvaleronitrile and an effective release promoting amount of a transport enhancing agent dispersed therein.

In another aspect of the invention, the objects of the invention are achieved by providing a transdermal drug delivery device comprising a permeable polymer matrix having an effective cardiovascular affecting amount of 5-[(3,4-dimethoxyphenethyl) methyl-amino]-2-(3, 4-dimethoxyphenyl)-2-isopropylvaleronitrile and an effective release promoting amount of a first transport enhancing agent dispersed therein, and a bioacceptable adhesive layer covering one face of said polymer matrix, said adhesive having an effective transport promoting amount of a second transport enhancing agent dispersed therein.

According to a still further aspect of the present invention, the objects of the invention are achieved by providing a transdermal drug delivery device comprising a permeable polymer matrix having an effective cardiovascular affecting amount of 5-[(3,4-dimethoxyphenethyl) methylamino]-2-(3,4-dimethoxyphenyl)-2-isopropylvaleronitrile and an effective release promoting amount of a transport enhancing agent dispersed therein, said polymer matrix having one surface disposable adjacent the skin of a patient, and a supply of skin permeation enhancing agent adjacent said one polymer matrix surface such that when said one surface is disposed adjacent (e.g. in intimate contact with) a patient's skin, the skin is then treated with said skin permeation enhancing agent.

In a particularly preferred embodiment, the transdermal drug delivery device of the invention comprises a matrix of bioacceptable cross-linked silicone polymer having an effective cardiovascular affecting amount of 5-[(3,4-dimethoxyphenethyl) methylamino]-2-(3,4-dimethoxyphenyl)-2-isopropylvaleronitrile and an effective release promoting amount of a first drug transport enhancing agent such as isopropyl myristate or N,N-diethyl-m-toluamide dispersed therein, said matrix having first and second opposed faces; a layer of bioacceptable silicone adhesive on said first face of said matrix, said adhesive having an effective drug transport promoting amount of a second transport enhancing agent dispersed therein, and an occlusive backing covering said second face of said matrix.

In a further preferred embodiment of the transdermal drug delivery device of the invention, an absorbent material impregnated with a skin permeation enhancing agent is removably positioned adjacent the adhesive surface of the drug delivery device such that the impregnated absorbent material can be peeled away prior to use and when peeled away will leave the adhesive surface moistened with skin permeation enhancing agent such that when the transdermal drug delivery device is applied to the skin of a patient, the skin surface will be moistened with the skin permeation enhancing agent.

BRIEF DESCRIPTION OF THE DRAWINGS

The invention will be described in further detail with reference to the accompanying drawings wherein.

DETAILED DESCRIPTION OF PREFERRED EMBODIMENTS

Figure 1:
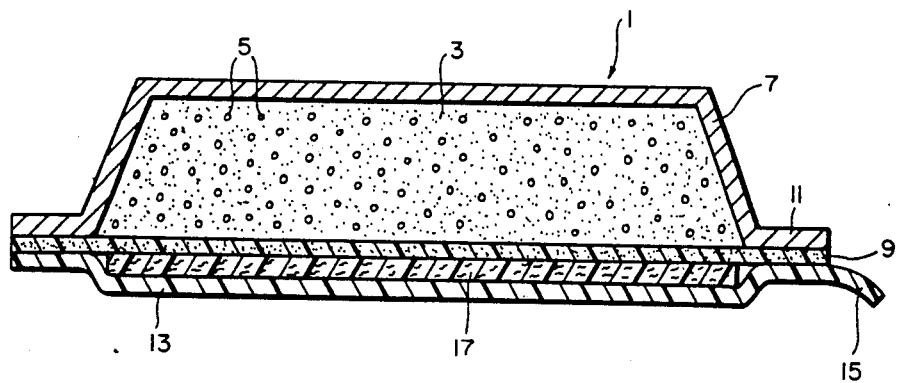
FIG. 1 is a schematic representation of matrix-type transdermal drug delivery device with a skin permeation enhancing agent reservoir removably disposed adjacent the adhesive layer.

The polymer matrix in which the active pharmaceutical is dispersed may be formed from any biocompatible polymeric material which exhibits significant lipophilic character. It has been found that release of active drug from the polymer matrix is better if the polymeric material of the matrix is essentially electroneutral with respect to the drug. That is to say, the polymer matrix must not donate any proton or electron to or receive any proton or electron from the active pharmaceutical, but instead the active pharmaceutical should exist essentially in electrically neutral, non-ionic form within the polymer matrix. Use of lipophilic (hydrophobic) polymer materials for the polymeric matrix also facilitates application of an adhesive over the surface of the matrix to secure the drug delivery device in continuous contact with the skin of a patient. Where hydrophilic polymer matrices are used, it is difficult to obtain satisfactory adhesion between the adhesive and the polymer matrix. Suitable bioacceptable polymers which can be used for preparation of the drug dispersing polymer matrix include silicone elastomers with various substituents on the silicon atoms, dialkylsiloxane-ethylene oxide copolymers, dialkylsiloxane-methacrylate copolymers, dialkylsiloxane-polycarbonate copolymers, ethylenevinyl acetate copolymers (EVA), polyolefins such as polyethylene or polypropylene, and other polymers with similar lipophilic, electroneutral character. Cross-linking silicone rubber materials such as silicone polymers corresponding to the formula:

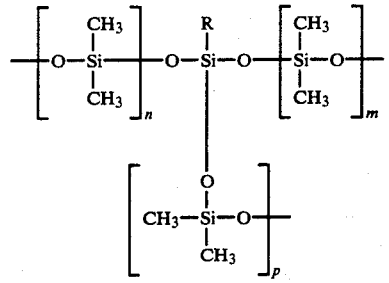

wherein R is alkoxy, alkyl, alkenyl or aryl containing 1 to 7 carbon atoms and wherein n, m and p are about 100 to 5,000 are particularly preferred as polymer matrix materials. Good results have been achieved using matricies formed of cross-linked polydimethyl siloxanes.

The thickness of the polymer matrix may be varied as desired depending inter alia upon the desired pharmaceutical dosage and duration of treatment. Ordinarily suitable matrix thicknesses may range from about 0.005 cm to about 0.5 cm.

An effective drug release promoting amount of a transport enhancing agent is desirably incorporated in the polymer matrix with the active pharmaceutical. Suitable transport enhancing materials include saturated aliphatic acids and derivatives such as myristic acid, isopropyl myristate, myristyl alcohol and mono-myristein; unsaturated aliphatic acids and derivatives such as oleic acid, propyl oleate, oleyl alcohol and mono-olein;

aryl alkyl tertiary amines including dialkyl aryl amines such as N,N-diethyl-m-toluamide; dialkyl sulfoxides such as dimethyl sulfoxide or decyl methyl sulfoxide; 1-substituted azacycloalkan-2-ones such as 1-dodecylazacycloheptan-2-one; dialkyl amides such as dimethyl or diethylacetoamide and thioglycollates such as calcium thioglycollate. Mixtures of two or more of the foregoing may be used to advantage; for example, mixtures of isopropyl myristate and N,N-diethyl-m-toluamide have been used to good effect.

The transport enhancing agent may be dispersed in the polymer matrix in amounts ranging from about 2 to about 40 percent by weight. Preferably, the transport enhancing agent will be present in an amount ranging from about 5 to about 30 percent by weight.

Where the polymer matrix is disposed in direct contact with the skin of a patient during use, the drug release promoting transport agent may also promote skin permeation by the drug.

The active pharmaceutical may be dispersed in the polymeric material prior to crosslinking to form the completed matrix. Alternatively, a solution or suspension of the active pharmaceutical in the transport enhancing agent may be dispersed in the polymer matrix prior to crosslinking in which case microreservoirs of the drug are formed in the matrix. Generally, the active drug will be present in an amount ranging from about 2 to about 50 percent by weight of the polymer matrix. Preferably, the amount of active drug will range from about 5 to about 30 weight percent with respect to the polymer matrix. Use of excessively low concentrations of active drug makes it difficult to obtain an acceptably high rate of release of the drug from the polymer matrix and to achieve a substantially uniform rate of release over an extended period of time. Use of excessively high concentrations of active drug renders it more difficult to control the rate of release of the drug from the matrix.

An occlusive backing material is disposed over one side of the polymer matrix. The backing material should be substantially impermeable to the active drug and any transport enhancer found in the polymer matrix. Such a backing is needed to prevent migration of the active ingredients from the polymer matrix other than to the skin of a patient to which the matrix is properly attached. Such a backing also facilitates handling of the drug delivery device and inhibits soiling of clothing worn by a patient over the transdermal drug delivery device. Suitable backing materials include metal foils such as aluminum foil, polyesters such as polyethylene terephthalate, polyamides such as polycaprolactones, polyolefins such as polyethylene or polypropylene, polyacrylates such as polymethylmethacrylate or acrylamide, polyurethanes, vinyl polymers and copolymers such as polyvinyl chloride or polyvinylacetate, polyurethanes, cellophanes or other similar materials. Multilayer laminates may also be used. A particularly preferred backing material comprises a skin-colored polyester film/metal foil laminate.

The drug delivery device of the invention may be advantageously secured to the skin of a patient by using a bioacceptable pressure-sensitive adhesive of the type used for medical dressings. In order to assure continuous and reliable contact between the drug-releasing polymer matrix and the patient's skin, it is preferred to apply the adhesive layer over at least the entire face of the polymer matrix. Suitable adhesive materials include non-toxic and non-irritating hypoallergenic adhesives based on polydienes, for example polybutadiene; acrylates, for example copolymers of methylacrylate or methacrylate and methacrylic acid; vinyl resins, for example polyvinylacetate, polyvinylalcohol, polyvinylchloride and copolymers of these and similar vinyl monomers; natural gums, for example guar or acacia; polyurethanes; and other adhesive materials. Silicone rubber adhesives have been found to combine excellent hypoallergenicity, satisfactory adhesion and good strippability when the patient is finished wearing the dressing and are therefore particularly preferred. Good results have been achieved using commercially available medical-grade polydimethylsiloxane adhesives.

Of course, it is also possible to provide adhesive only around the periphery of the drug delivery device of the invention to secure it to the patient or even to omit the adhesive layer entirely and secure the drug delivery device to the patient with any overlying wrap or bandage.

The interposed adhesive between the drug releasing polymer matrix and the skin of the patient will to some extent impede the transfer of the drug from the matrix to the patient. However, it has been found that by incorporating a suitable transport enhancing agent into the adhesive, good transfer of the drug from the matrix to the patient may be obtained. Any of the transport enhancing agents listed above as suitable for inclusion in the polymer matrix may also be used in the adhesive. It is not necessary that the same transport enhancing agent be used in the adhesive as is used in the polymer matrix. For verapamil, particularly preferred transport enhancing agents include isopropyl myristate, n-decylmethylsulfoxide, oleyl alcohol, propyl oleate, 1-dodecylazacycloheptan-2-one, or N,N-diethyl-m-toluamide. From about 1 to about 30 percent by weight transport enhancing agent may be incorporated into the adhesive. Preferably, the amount of transported into the adhesive. Preferably, the amount of transport enhancing agent will lie in the range from about 5 to about 25 weight percent of the adhesive.

The pH of the adhesive has also been found to affect the transfer of the active drug from the drug-releasing matrix to the patient. The pH of the adhesive should be such that the active drug exists as an electrically neutral species at the interfaces between the matrix and adhesive and between the adhesive and the skin of the patient. Suitable control of the pH achieves an optimum balance between drug solubility which increases the rate of release of the drug from the polymer matrix and skin hydration which increases the rate of absorption of the drug species through the skin. The optimum pH may vary somewhat with different drugs. For verapamil, the pH should be maintained between about 5 and about 7. It is particularly preferred that the pH of the adhesive system in the verapamil transdermal delivery device of the invention be maintained at approximately 6. If desired, a small amount of a buffering agent such as a disodium hydrogen phosphate/citric acid buffer may be incorporated into the adhesive and/or polymer matrix to assist in maintaining the desired pH value at which the drug molecules exist in electrically neutral form.

The adhesive layer may be applied to the exposed face of the polymer matrix and the protruding margins of the backing by solvent casting or spraying. Any suitable solvent may be used such as acetone, methyl ethyl acetate, diethyl ether, etc. Dispersion of a skin permeation enhancing agent and/or a buffering agent throughout the adhesive may be achieved by dissolving the agent in the adhesive solution prior to applying the adhesive to the polymer matrix. The thickness of the applied adhesive layer may vary. Suitable thicknesses may range from about 10 to about 200 microns or more. In order to minimize any tendency of the adhesive layer to impede transfer of the pharmaceutical substances from the polymer matrix to a patient's skin, it is generally desirable that the adhesive layer be as thin as practicable.

Prior to use of the drug delivery device the adhesive layer may be covered by a releasable protective strip. Such a strip may be formed from the same materials used for the backing provided with a conventional release coating, for example, a fluorocarbon ywc, Kt (6/28/85) or a silicone surface treatment.

It has also been found that absorption of the active drug through the skin can be enhanced by pretreating the skin with a permeation enhancing agent when the drug delivery device is applied to the skin of the patient. Any of the transport enhancing agents described above may be utilized. Particularly good results have been obtained for verapamil using n-decyl-methylsulfoxide, 1-dodecylazacycloheptan-2-one, isopropyl myristate or N,N-diethyl-m-toluamide. Pretreatment may be achieved by simply contacting or wiping the skin with the permeation enhancing agent shortly prior to affixing the drug delivery device to the patient's skin. Alternatively, a reservoir of transport enhancing agent may be included in the drug delivery device such that the skin is moistened with the transport enhancing agent as the drug delivery device is applied to the patient.

Typically, permeation of the drug through the stratum corneum (i.e. the outermost layer of the epidermis) is quite slow. If the stratum corneum is untreated, it may limit the rate at which the active drug can be administered to the patient. Under such circumstances, it is often desirable that the rate of drug release from the polymer matrix be slightly greater than the rate of permeation through the stratum corneum so that the surface of the skin will be saturated with the active drug in order to maximize the rate of drug absorption.

If, on the other hand, the skin is appropriately treated with a skin permeation enhancing agent either by pretreatment or by incorporation of sufficient permeation enhancing agent into the adhesive layer, it is possible to increase the rate of skin permeation to a value which equals or exceeds the desired rate of transfer of active drug to the patient. Under such circumstances, skin permeation is no longer the rate-limiting step. Instead, the overall rate of transfer of the active drug to the patient is controlled by the rate of release of the drug from the drug delivery device. This is particularly desirable in situations where the rate of skin permeation is affected by patient differences so that uniform dosing can be achieved independently of the nature or condition of the patient's skin.

The size of the drug delivery device should be large enough to permit easy handling but small enough to facilitate convenient application to the patient and to avoid an obstrusive appearance. Typical sizes may range from about 3 square centimeters to about 100 square centimeters, preferably from about 5 square centimeters to about 80 square centimeters. It is understood, of course, that the size of the delivery device must be interrelated with the rates of release and absorption of the active drug in order to achieve administration of a desired dosage to the patient.

The desired dosage will vary depending on the individual drug as well as on the size and condition of the patient. For verapamil, suitable dosages may lie in the range from about 1 to about 200 milligrams per day. In most cases, the verapamil dosage will lie in the range from about 1 to about 100 milligrams per day. The transdermally absorbed verapamil dosage will generally lie in the range from about 2 to about 20 milligrams per day. Dosages in the range from about 5 to about 10 milligrams per day are usually preferred. The actual dosage which should be administered in any given case can be determined by the prescribing physician in accordance with good medical practice. If desired, higher rates of administration can be achieved by affixing more than one transdermal drug delivery device to the patient.

Generally speaking, the matrix will contain some excess of drug above the dosage amount to be administered to the patient. Ordinarily the polymer matrix will contain from about 1.5 to about 10 times the intended dosage amount, preferably from about 2 to about 5 times the dosage amount of drug which is to be transdermally absorbed. The drug may also be incorporated in the form of an active derivative or a prodrug.

Referring now to the drawings, FIG. 1 illustrates a first preferred embodiment of the transdermal drug delivery device of the invention generally designated by reference numeral 1. The device comprises a permeable lipophilic cross-linked polymer matrix 3 having an effective release-promoting amount of a transport enhancing agent dispersed throughout the matrix. Also dispersed throughout the matrix is a pharmaceutically effective amount of a transdermally absorbable drug represented schematically by particles 5. The back of the polymer matrix is covered by an occlusive layer, such as plastic film/metal foil laminate 7, to prevent loss of material through the back of the drug delivery device and to protect the device from the environmental conditions. A layer of bioacceptable pressure-sensitive adhesive 9 is applied to the opposite face of the polymer matrix and extends over the margins 11 of the backing. A suitable amount of transport enhancing agent is also dispersed in adhesive layer 9. The outer face of the adhesive is covered by a releasable cover strip 13 provided with a protruding pull tab 15. In the illustrated embodiment, an absorbent layer 17 is affixed to cover layer 13 between the cover layer and adhesive layer 9. For example, the absorbent layer could comprise an open-celled foam layer which has been heat sealed to the inner surface of the cover layer. Absorbent layer 17 is impregnated with a permeation enhancing agent in order to facilitate pretreatment of the patient's skin.

In use, tab 15 is firmly grasped and pulled away from adhesive layer 9 to separate the cover 13 and absorbent layer 17 from the rest of the drug delivery device. As the absorbent layer 17 separates from the adhesive layer, a thin film of permeation enhancing agent remains on the surface of the adhesive layer. The exposed adhesive surface is then pressed against the skin of a patient to be treated with the drug contained in the drug delivery device. The adhesive adheres to the skin and thereby holds the entire surface of the drug delivery device in contact with the patient. As the adhesive is applied to the patient's skin, the skin surface is moistened by the thin film of transport enhancing agent on the surface of the adhesive, thereby facilitating increased premeation of the active drug through the stratum corneum. If desired, the surface of the patient's skin may be wiped with the transport enhancing agent-containing absorbent layer to effect further pretreatment of the skin before the drug delivery device is affixed.

The active drug substance diffuses at a substantially controlled rate from the polymer matrix through the thin adhesive layer and permeates through the outer layers of skin into the dermis where it is absorbed through the fine capillary network of the papillary layer and enters the blood stream. The drug substance is carried by the blood throughout the body of the patient to achieve a systemic treatment.

Figure 2:
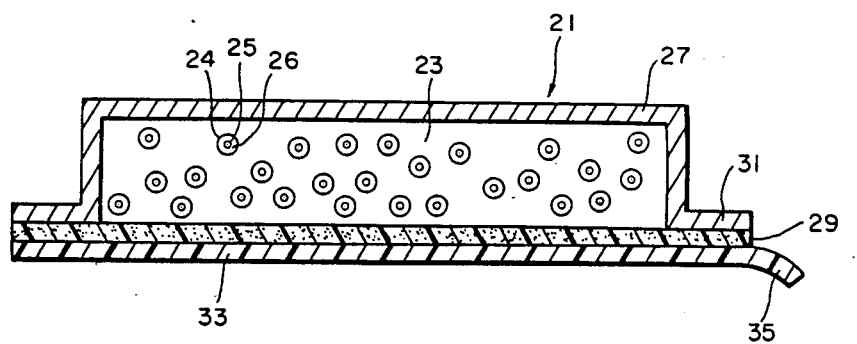
FIG. 2 is a schematic representation of a microreservoir-type transdermal drug delivery device.

FIG. 2 is a schematic representation of an alternative transdermal drug delivery device embodiment generally designated by reference numeral 21. Dispersed throughout polymer matrix 23 are microreservoirs 24 containing active drug 25 dissolved or dispersed in a transport-enhancing agent 26. Use of the microreservoir-type matrix structure is particularly advantageous where it is desired to incorporate a larger proportion of active drug into the polymer matrix than can be readily dispersed uniformly throughout the matrix. The back of the polymer matrix is covered by an occlusive backing layer 27, and a biocompatible pressure-sensitive adhesive layer 29 is disposed over the opposite face of the matrix and the margins 31 of the backing layer. The adhesive layer is in turn covered with a releasable cover layer 33 which is separated from the device to expose the adhesive prior to use by pulling on tab 35.

The manner of use of the embodiment of FIG. 2 is similar to that described above for the embodiment of FIG. 1. It is understood, of course, that the embodiment of FIG. 2 could also be provided, if desired, with a reservoir of transport enhancing agent between adhesive layer 29 and cover layer 33 in order to effect a permeation-enhancing pretreatment of the patient's skin when the drug delivery device is applied to the patient.

It should be understood, of course, that the drawings are merely schematic representations of drug delivery devices according to the invention in which proportions have been exaggerated for purposes of illustration.

Further details of the invention will become apparent from a consideration of the following nonlimiting illustrative examples.

EXAMPLE 1

Silicone elastomer (Dow Corning Silastic medical-grade 382) was thoroughly mixed with isopropyl myristate using a laboratory agitator at 1,000 rpm for three minutes. Verapamil base was then incorporated into the mixture and mixing was continued for four additional minutes. Then a few drops of stannous octanoate cross-linking catalyst were added and thoroughly mixed for another minute. The mixture was deaerated under vacuum for five minutes. The deaerated mixture was pressed into sheets 0.015 centimeters thick.

Diffusion of the active pharmaceutical was tested using a Valia-Chien diffusion cell. See P.R. Keshary and Y.W. Chien, in Drug Develop. and Ind. Pharm., 10, (6) 883–913 (1984). The freshly excised abdominal skin of female hairless mouse (5 to 7 weeks old), which has been found to approximate the transdermal absorption behavior of human skin, was clamped over the receptor cell, and the verapamil-containing polymer matrix was disposed against the stratum corneum of the skin. The receptor compartment was filled with a buffer solution at a pH of 7.4 to simulate the physiologic pH of the dermal fluid. The temperature of the system was controlled at 37° C. throughout the experiment. The receptor solution was sampled periodically and analyzed by high pressure liquid chromatography to determine how much of the active drug from the polymer matrix had been absorbed through the skin and the rate of skin permeation was calculated.

The rates of skin permeation of verapamil at different loading doses of verapamil and isopropyl myristate are shown in the following table:

| Device Number | Verapamil Concentration (weight percent) | Isopropyl myristate Concentration (weight percent) | Permeation Rate $\mu g/cm^2$-hr |
| --- | --- | --- | --- |
| VPS17 | 4.2 | 4.2 | 13.94 |
| VPS18 | 8.4 | 4.2 | 14.04 |
| VPS19 | 8.4 | 8.4 | 21.63 |
| VPS21 | 8.4 | 8.4 | 23.34 |
| VPS22 | 8.4 | 12.6 | 39.88 |
| VPS23 | 12.6 | 12.6 | 66.92 |

EXAMPLE 2

Verapamil base and isopropyl myristate were thoroughly mixed using a laboratory agitator at 1,000 rpm for three minutes. The resulting co-solvent mixture was then incorporated into silicone elastomer (Dow Corning Silastic medical-grade 382) and mixed for four additional minutes. One drop of catalyst for the silicone elastomer was then added and mixed for another minute. The catalyzed mixture was deaerated under vacuum for five minutes, and the deaerated mixture was pressed into sheets 0.015 centimeters thick to form a microreservoir type polymer matrix.

The rate of skin permeation of verapamil was measured as described above. For a microreservoir-type matrix containing 4.2 weight percent verapamil and 4.2 weight percent isopropyl myristate the rate of permeation was found to be 12.04 $\mu g/cm^2$-hr (micrograms per square centimeter per hour) For a microreservoir-type polymer matrix containing 7 weight percent verapamil and 7 weight percent isopropyl myristate the rate of verapamil skin permeation was found to be 13.94 $\mu/cm^2$-hr.

EXAMPLE 3

The procedure of Example 2 was repeated except that 40% polyethylene glycol 400 was utilized as the co-solvent instead of isopropyl myristate. For a microreservoir-type polymer matrix containing 4.2 weight percent verapamil and 4.2 weight percent polyethylene glycol 400 (40%) the rate of verapamil skin permeation was found to be 4.51 micrograms per square centimeter per hour.

EXAMPLE 4

The procedure of Example 2 was repeated except glycerol was utilized as the co-solvent instead of isopropyl myristate. For a microreservoir type polymer matrix containing 9.1 weight percent verapamil and 9.1 weight percent glycerol, the rate of verapamil skin permeation was found to be 6.87 micrograms per square centimeter per hour.

EXAMPLE 5

The procedure of Example 3 was repeated except 1-dodecylazacycloheptan-2-one (AZONE, Nelson Research and Development) was additionally added as a transport enhancing agent. For a microreservoir type polymer matrix containing 9.2 weight percent verapamil, 9.2 weight percent polyethylene glycol 400 (40%) and 5 weight percent 1-dodecylazacycloheptan-2-one, the rate of verapamil skin permeation was found to be 11.56 micrograms per square centimeter per hour.

EXAMPLE 6

The procedure of Example 1 was repeated except that a thin layer of a pressure-sensitive silicone adhesive (Dow Corning DC355) was applied to the surface of the polymer matrix and used to adhere the polymer matrix to the skin. For a matrix-type delivery system containing 4.2 weight percent verapamil and 4.2 weight percent isopropyl myristate the rate of skin permeation was found to decrease to 11.06 micrograms per square centimeter per hour.

EXAMPLE 7

The procedure of Example 6 was repeated except 5% 1-dodecylazacycloheptan-2-one transport enhancing agent was intimately blended into the adhesive polymer solution before application to the polymer matrix. The resulting verapamil skin permeation data is shown in the following table:

| Delivery Device Number | Verapamil Concentration (weight percent) | Isopropyl Myristate Concentration (weight percent) | Permeation Rate $\mu g/cm^2$-hr |
|---|---|---|---|
| VPS17c | 4.2 | 4.2 | 18.58 |
| VPS18c | 8.4 | 4.2 | 17.82 |
| VPS19c | 8.4 | 8.4 | 20.09 |

EXAMPLE 8

The procedure of Example 1 was repeated except polyethylene glycol 400 (40%) and 5% 1-dodecylazacycloheptane-2-one were utilized as the transport enhancing agent instead of isopropyl myristate. The resulting matrix-type delivery device containing 4.2 weight percent verapamil showed a permeation rate of 9.13 micrograms per square centimeter per hour. A similar delivery system containing 9.2 weight percent verapamil yielded a permeation rate of 11.56 micrograms per square centimeter per hour.

EXAMPLE 9

The procedure of Example 8 was repeated except the skin outer surface was pretreated with 1-dodecylazacycloheptan-2-one prior to application of the drug delivery matrix by placing an absorbent pad impregnated with 1-dodecylazacycloheptan-2-one on the skin for about 15 to 30 seconds where the drug delivery device is subsequently applied. The verapamil permeation rate for the matrix type device containing 4.2 weight percent verapamil increased to 11.48 micrograms per square centimeter per hour while that for the device containing 9.2 weight percent verapamil increased to 17.26 micrograms per square centimeter per hour.

EXAMPLE 10

The procedure of Example 1 was repeated except that the skin was pretreated with isopropyl myristate prior to application of the drug delivery matrix by placing an isopropyl myristate impregnated absorbent pad on the skin for about 15 to 30 seconds where by drug delivery device is subsequently applied. The resulting skin permeation rates are listed in the following table:

| Delivery Device Number | Verapamil Concentration (weight percent) | Enhancer Concentration (weight percent) | Permeation Rate $\mu g/cm^2$-hr |
|---|---|---|---|
| VPS18e | 4.2 | 8.4 | 45.00 |
| VPS19e | 8.4 | 8.4 | 58.57 |
| VPS22d | 8.4 | 12.6 | 58.68 |
| VPS23d | 12.6 | 12.6 | 112.38 |
| VPS25d | 12.6 | 8.4 | 41.62 |

EXAMPLE 11

The procedure of Example 6 was repeated except isopropyl myristate transport enhancing agent was intimately blended with the adhesive prior to application of adhesive to the drug-containing polymer matrix. The permeation rates achieved with the resulting drug delivery devices are summarized in the following table:

| Delivery Device Number | Verapamil Concentration (weight percent) | Enhancer Concentration (weight percent) | Enhancer Concentration Adhesive (weight percent) | Permeation Rate $\mu g/cm^2$-hr |
|---|---|---|---|---|
| VPS21b | 8.4 | 8.4 | 10 | 32.40 |
| VPS21c | 8.4 | 8.4 | 20 | 39.79 |
| VPS23a | 12.6 | 12.6 | 5 | 30.52 |
| VPS23b | 12.6 | 12.6 | 10 | 43.61 |
| VPS23c | 12.6 | 12.6 | 20 | 71.38 |

EXAMPLE 12

The procedure of Example 1 was repeated except N,N-diethyl-m-toluamide (DEET) was utilized as the transport enhancing agent instead of isopropyl myristate. The verapamil skin permeation rates achieved are listed in the following table:

| Delivery Device Number | Verapamil Concentration (weight percent) | Enhancer Concentration (weight percent) | Permeation Rate $\mu g/cm^2$-hr |
|---|---|---|---|
| VPS24 | 8.4 | 8.4 | 98.39 |
| VPS45 | 10 | 20 | 180.25 |
| VPS46 | 5 | 20 | 200.12 |
| VPS47 | 10 | 30 | 284.25 |
| VPS48 | 20 | 20 | 121.96 |

EXAMPLE 13

The procedure of Example 1 was repeated except propyl oleate was used as the transport enhancing agent instead of isopropyl myristate. The verapamil skin permeation rate achieved by a polymer matrix containing 10 weight percent verapamil and 10 weight percent propyl oleate was 20.27 micrograms per square centimeter per hour.

EXAMPLE 14

The procedure of Example 13 was repeated except oleyl alcohol was utilized as the transport enhancing agent instead of propyl oleate. The verapamil skin permeation rate achieved by a polymer matrix containing 10 weight percent verapamil and 10 weight percent oleyl alcohol was 36.26 micrograms per square centimeter per hour.

EXAMPLE 15

The procedure of Example 14 was repeated except n-decylmethylsulfoxide (DMS) was used as the transport enhancing agent instead of oleyl alcohol. The verapamil skin permeation rate achieved by a polymer matrix containing 10 weight percent verapamil and 10 weight percent DMS was 105.28 micrograms per square centimeter per hour.

EXAMPLE 16

The procedure of Example 1 was repeated except mixtures of isopropylmyristate (IPM) and N,N-diethyl-m-toluamide (DEET) were utilized as the transport enhancing agent. The resulting skin permeation rates are listed in the following table:

| Delivery Device Number | Verapamil Concentration (weight percent) | Enhancer Concentration (weight percent) | | Permeation Rate $\mu g/cm^2$-hr |
|---|---|---|---|---|
| | | IPM | DEET | |
| VPS39 | 10 | 10 | 10 | 139.55 |
| VPS40 | 10 | 5 | 15 | 164.04 |

EXAMPLE 17

A matrix-type transdermal drug delivery device is prepared by intimately blending equal weights of verapamil and N,N-diethyl-m-toluamide after which the mixture is uniformly dispersed in a bioacceptable silicone elastomer. Crosslinking catalyst is then added to the elastomer, the catalyzed mixture is deaerated, and the deaerated mixture is pressed into thin sheets 0.015 centimeters thick. The resulting sheets are cut into 5 centimeter diameter circles. One face of each circle is covered with an occlusive backing comprising an aluminum foil/polyester film laminate (3M Company, soctchpak 1006). A bioacceptable, amine-resistant silicone adhesive (Dow Corning X7-2920) containing 20 weight percent N,N-diethyl-m-toluamide intimately blended therewith is applied to the opposite face of the polymer matrix. The adhesive surface is then covered with a removable polyethylene film having an absorbent open-celled foam layer heat sealed to its inner face and saturated with N,N-diethyl-m-toluamide.

EXAMPLE 18

Equal amounts of verapamil base and isopropyl myristate were thoroughly mixed using a laboratory agitator at 1000 r.p.m. for three minutes. The resulting cosolvent mixture was then incorporated into a silicone elastomer (Dow Corning Silastic medical-grade 382) and mixed for four additional minutes. One drop of catalyst for the silicone elastomer was then added and mixed for another minute. The catalyzed mixture was deaerated under vacuum for five minutes, and the deaerated mixture was pressed into sheets 0.015 centimeters thick to form a microreservoir-type polymer matrix containing 13 weight percent verapamil base and 13 weight percent isopropyl myristate transport enhancing agent. The sheets were cut into 20 square centimeter patches, and the back of each patch was adhered to the center of an occlusive metal foil backing sheet (3M Company) with a silicone adhesive (Dow Corning DC 355). The front surface of each patch was covered with a thin layer of silicone adhesive (Dow Corning DC 355) into which 20 weight percent isopropyl myristate transport enhancing agent had been incorporated. Prior to use of the device, the exposed adhesive surfaces on the face of the polymer matrix and the margins of the backing sheet were temporarily covered with a protective release liner.

In use, the release liner was stripped away, and from two to four patches were applied to the chest areas of healthy male volunteers 21 to 40 years of age. In some cases the patient's skin was pretreated by contact with an absorbent pad saturated with isopropyl myristate for a few seconds prior to applying the patches. Patches were removed after 24 hours. Effective transdermal administration of verapamil was confirmed by monitoring the heart rate, blood pressure, respiration and ECG of each patient and by withdrawing and analyzing blood samples just prior to application of the patches and periodically over 48 hours after application of the patches.

The foregoing description and examples have been set forth merely to illustrate the invention and are not intended to be limiting. Since modifications of the described embodiments incorporating the spirit and substance of the invention may occur to persons skilled in the art, the scope of the invention is to be limited solely with respect to the appended claims and equivalents.

What is claimed is:

1. A transdermal drug delivery device comprising:
   a permeable polymer matrix comprising a silicone elastomer corresponding to the formula:

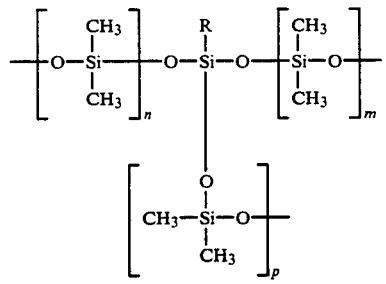

wherein R represents an alkoxy, alkyl, alkenyl or aryl group containing 1 to 7 carbon atoms and wherein n, m and p are each 100 to 5,000; said permeable polymer matrix having an effective cardiovascular affecting amount of 5-[-(3,4-dimethoxyphenyl) methylamino]-2-(3,4-dimethoxyphenly)-2-isopropylvaleronitrile and an effective release promoting amount of a first transport enhancing agent dispersed therein, and
   a bioacceptable adhesive layer covering one face of said polymer matrix, said adhesive having an effective drug transport promoting amount of a second transport enhancing agent dispersed therein;
   wherein said second agent is different from said first agent.

2. A transdermal drug delivery device as recited in claim 1, wherein said first and second transport enhancing agents are independently selected from the group consisting of lower alkyl esters of saturated and unsaturated fatty acids, mineral oil, dialkylsulfoxides, N,N-dialkylamides, N-alkyl azacyclo ketones, thioglycolate salts, fatty alcohols, saturated and unsaturated fatty acids, glycol monoesters of fatty acids, and fatty acid monoglycerides.

3. A transdermal drug delivery device as recited in claim 2, wherein said first and second transport enhancing agents are the same.

4. A transdermal drug delivery device as recited in claim 2, wherein said adhesive has a pH in the range from about 5 to about 7.

5. A transdermal drug delivery device according to claim 4, wherein the pH of said adhesive is about 6.

6. A transdermal drug delivery device as recited in claim 2, wherein said adhesive layer comprises from about 1 to about 30 weight percent transport enhancing agent.

7. A transdermal drug delivery device as recited in claim 6, wherein said adhesive layer comprises from about 5 to about 25 weight percent transport enhancing agent.

8. A transdermal drug delivery device as recited in claim 2, wherein said second transport enhancing agent comprises isopropyl myristate.

9. A transdermal drug delivery device as recited in claim 2, wherein said first transport enhancing agent comprises N,N-diethyl-m-toluamide.

10. A transdermal drug delivery device as recited in claim 2, wherein said adhesive comprises a bioacceptable silicone elastomer.

11. A transdermal drug delivery device comprising a permeable bioacceptable lipophilic polymer matrix having an effective cardiovascular affecting amount of 5-[-(3,4-dimethoxyphenyl)methylamino]-2-(3,4-dimethoxyphenyl)-2-isopropylvaleronitrile and an effective release promoting amount of a transport enhancing agent dispersed therein, said polymer matrix being substantially electroneutral with respect to said 5-[-(3,4-dimethoxyphenylethyl)methylamino]-2-(3,4-dimethoxyphenyl)-2-isopropylvaleronitrile.

12. A transdermal drug delivery device as recited in claim 11 wherein said polymer matrix comprises a silicone elastomer corresponding to the formula:

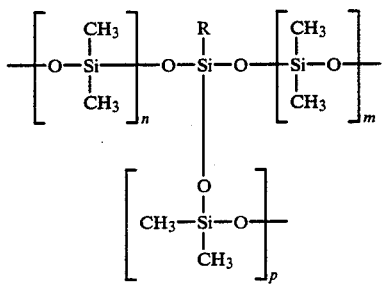

wherein R represents an alkoxy, alkyl, alkenyl or aryl group containing 1 to 7 carbon atoms and wherein n, m and p are each 100 to 5,000.

13. A transdermal drug delivery device as recited in claim 11 wherein said transport enhancing agent is selected from the group consisting of lower alkyl esters of saturated and unsaturated fatty acids, mineral oil, dialkylsulfoxides, N,N-dialkylamides, N-alkyl azacyclo ketones, thioglycolate salts, fatty alcohols, saturated and unsaturated fatty acids, glycol monoesters of fatty acids, and fatty acid mono-glycerides.

14. A transdermal drug delivery device as recited in claim 13, wherein said transport enhancing agent comprises from about 2 to about 50 weight percent of said polymer matrix.

15. A transdermal drug delivery device as recited in claim 14, wherein said transport enhancing agent comprises from about 5 to about 30 weight percent of said polymer matrix.

16. A unit-dose package comprising a transdermal drug delivery device comprising a permeable bioacceptable lipophilic polymer matrix having an effective cardiovascular affecting amount of 5-[(3,4-dimethoxyphenethyl) methylamino]-2-(3,4-dimethoxyphenyl)-2-isopropylvaleronitrile and an effective release promoting amount of a transport enhancing agent dispersed therein, and means for pretreating the skin of a patient with a skin permeation enhancing agent prior to application of said transdermal drug delivery device to the skin of the patient.

17. A unit-dose package as recited in claim 16, wherein said skin permeation enhancing agent is selected from the group consisting of lower alkyl esters of saturated and unsaturated fatty acids, mineral oil, dialkylsulfoxides, N,N-dialkylamides, N-alkyl azacyclo ketones, thioglycolate salts, fatty alcohols, saturated and unsaturated fatty acids, glycol monoesters of fatty acids, and fatty acid monoglycerides.

18. A transdermal drug delivery device comprising:
a permeable polymer matrix having an effective cardiovascular affecting amount of 5-[(3,4-dimethoxyphenyl)-methylamino]-2-(3,4-dimethoxyphenyl)-2-isopropylvaleronitrile and an effective release promoting amount of a transport enhancing agent dispersed therein, said drug delivery device having one surface disposable adjacent the skin of a patient in use;
a protective layer covering said one surface prior to use of said drug delivery device and strippable therefrom when it is desired to use said drug delivery device, and
a supply of skin permeation enhancing agent disposed between said one surface and said protective layer such that when said protective layer is stripped from said device and said one surface is disposed adjacent a patient's skin, the skin is directly contacted by said supply of skin permeation enhancing agent.

19. A transdermal drug delivery device as recited in claim 18, wherein an adhesive layer is provided over said polymer matrix to secure the polymer matrix to the skin of a patient and said supply of skin permeation enhancing agent is disposed between said adhesive layer and the strippable protective layer.

20. A transdermal drug delivery device as recited in claim 19, wherein said supply of skin permeation enhancing agent comprises a removable absorbent layer covering said adhesive layer and impregnated with said skin permeation enhancing agent.

21. A transdermal drug delivery device as recited in claim 18, further comprising an occlusive backing covering the surface of said matrix opposite said surface which is disposable adjacent the skin of a patient.

22. A transdermal drug delivery device as recited in claim 18 wherein said polymer matrix comprises a silicone elastomer corresponding to the formula:

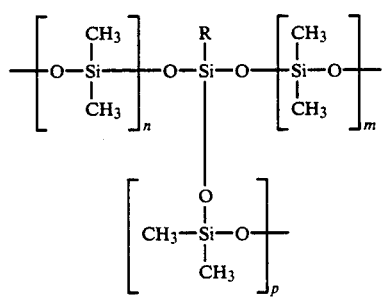

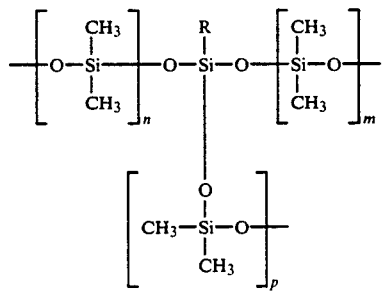

wherein R represents an alkoxy, alkyl, alkenyl or aryl group containing 1 to 7 carbon atoms and wherein n, m and p are each 100 to 5,000.

23. A transdermal drug delivery device as recited in claim 18 wherein said skin permeation enhancing agent is selected from the group consisting of lower alkyl esters of saturated and unsaturated fatty acids, mineral oil, dialkylsulfoxides, N,N-dialkylamides, N-alkyl azacyclo ketones, thioglycolate salts, fatty alcohols, saturated and unsaturated fatty acids, glycol monoesters of fatty acids, and fatty acid monoglycerides.

24. A transdermal drug delivery device comprising:
a permeable lipiphilic polymer matrix having an effective cardiovascular affecting amount of 5-[(3,4-dimethoxyphenethyl) methylamino]-2-(3,4-dimethoxyphenyl)-2-isopropylvaleronitrile dispersed therein, and
a bioacceptable adhesive layer covering a face of said polymer matrix, said adhesive having an effective drug transport promoting amount of a transport enhancing agent dispersed therein and having a pH at which said 5-(3,4-dimethoxyphenethyl) methylamino]-2-(3,4-dimethoxyphenyl)-2-isopropylvaleronitrile exists as an electrically neutral species.

25. A transdermal drug delivery device according to claim 24, wherein said adhesive further comprises a buffering agent for maintaining said pH.

26. A transdermal drug delivery device comprising:
a permeable silicone elastomer matrix corresponding to the formula:

in which R represents an alkoxy, alkyl, alkenyl or aryl group containing 1 to 7 carbon atoms and wherein n, m and p are each 100 to 5,000 and having an effective cardiovascular affecting amount of 5-[(3,4-dimethoxyphenethyl) methylamino]-2-(3,4-dimethoxyphenyl)-2-isopropylvaleronitrile and an effective release promoting amount of a first transport enhancing agent intimately dispersed therein, and
a bioacceptable adhesive layer having an effective drug transport promoting amount of a second transport enhancing agent dispersed therein, said adhesive layer having a first face disposed in contiguous face to face contact with a face of said matrix and a second face opposite said first face disposable in contact with skin of a person to whom it is desired to transdermally administer 5-[(3,4-dimethoxyphenethyl) methylamino]-2-(3,4-dimethoxyphenyl)-2-isopropylvaleronitrile.

27. A transdermal drug delivery device according to claim 26, wherein said adhesive layer has a pH at which 5-[(3,4-dimethoxyphenethyl) methylamino]-2-(3,4-dimethoxyphenyl)-2-isopropylvaleronitrile exists as an electrically neutral species.

28. A transdermal drug delivery device as recited in claim 27, wherein said first transport enhancing agent comprises N,N-diethyl-m-toluamide.

29. A transdermal drug delivery device comprising:
a permeable polymer matrix having an effective cardiovascular affecting amount of 5-[(3,4-dimethoxyphenethyl)-methylamino]-2-(3,4-dimethoxyphenyl)-2-isopropylvaleronitrile and an effective release promoting amount of a transport enhancing agent dispersed therein, said
polymer matrix having one surface disposable adjacent the skin of a patient, and
a supply of skin permeation enhancing agent adjacent said one polymer matrix surface such that when said one surface is disposed adjacent a patient's skin, the skin is directly contacted by said supply of skin permeation enhancing agent,
wherein said supply of skin permeation enhancing agent comprises a film of skin permeation enhancing agent on the surface of an adhesive layer.

* * * * *